United States Patent
Gan

(10) Patent No.: US 7,999,931 B2
(45) Date of Patent: *Aug. 16, 2011

(54) PACKAGING OR CONTAINER WITH OPTICAL INDICATOR

(75) Inventor: Livne Gan, Medereshet Ben Gurion (IL)

(73) Assignee: Virtue Sense Ltd., Rosh Hain (IL)

( * ) Notice: Subject to any disclaimer, the term of this patent is extended or adjusted under 35 U.S.C. 154(b) by 574 days.

This patent is subject to a terminal disclaimer.

(21) Appl. No.: 11/791,517

(22) PCT Filed: Apr. 19, 2005

(86) PCT No.: PCT/IL2005/000409
§ 371 (c)(1),
(2), (4) Date: Sep. 2, 2008

(87) PCT Pub. No.: WO2005/101971
PCT Pub. Date: Nov. 3, 2005

(65) Prior Publication Data
US 2009/0128803 A1  May 21, 2009

Related U.S. Application Data

(60) Provisional application No. 60/563,463, filed on Apr. 20, 2004.

(51) Int. Cl.
*G01N 21/41* (2006.01)
(52) U.S. Cl. .................................................. 356/128
(58) Field of Classification Search .................. 356/128
See application file for complete search history.

(56) References Cited

U.S. PATENT DOCUMENTS

| 4,569,590 A | 2/1986 | Karny et al. |
| 2008/0309937 A1* | 12/2008 | Gan ........................ 356/364 |

FOREIGN PATENT DOCUMENTS

| EP | 1324015 | 7/2003 |
| GB | 1 508 783 | 4/1978 |
| WO | WO 2005/050179 | 6/2005 |

OTHER PUBLICATIONS

IBM Technical Disclosure Bulletin, "Automated Detector for Liquid Chromotography", Sep. 1976, vol. 19, No. 4.*
International Search Report for International Application No. PCT/IL05/00409 mailed Mar. 9, 2006.

* cited by examiner

*Primary Examiner* — Roy Punnoose
(74) *Attorney, Agent, or Firm* — Pearl Cohen Zedek Latzer, LLP

(57) ABSTRACT

An optical indicator (130) for identification of a changed state of a fluid with respect to a reference state of the same fluid, or for monitoring or checking or authenticating a fluid. The fluid has an optical parameter that changes with the change of the state of the fluid. The optical indicator (130) may be attached to or integral with a container or packaging (132) for the fluid. The indicator (130) includes a cavity configured to be filed with the fluid such that the fluid filled cavity forms a variable optical element having an optical performance that varies depending on the changeable fluid's optical parameter. The fluid filled cavity coupled to other optical components of the indicator provides an image that may be compared to a reference image to detect a change of at least one optical property of the fluid as compared to the reference fluid. The comparison may be performed visually or by a suitable detector. The comparison may include automated processing of the detector's output signal(s).

31 Claims, 8 Drawing Sheets

Changed

Changed

PACKAGING OR CONTAINER WITH OPTICAL INDICATOR

CROSS-REFERENCE TO RELATED APPLICATIONS

This application is a National Phase Application of PCT International Application No. PCT/IL2005/000409, entitled "Packaging or Container with Optical Indicator", International Filing Date Apr. 19, 2005, published on Nov. 3, 2005 as International Publication No. WO 2005/101971, which in turn claims priority from US Provisional Patent Application No. 60/563,463, filed Apr. 20, 2004, both of which are incorporated herein by reference in their entirety.

FIELD OF THE INVENTION

This invention relates generally to indicators of a condition of a fluid based on optical properties of the fluid and to packaging or containers including such optical indicators and methods of constructing them.

BACKGROUND OF THE INVENTION

U.S. Pat. No. 4,569,590 to Karney describes a system for determining unknown index of refraction of a sample fluid with reference to the refraction index of a known reference fluid. The system comprises a collimated light source, a light pervious cell formed as a biconvex lens fillable with a fluid, a pair of gratings and a screen. Collimated light is directed through the cell filled first with the reference fluid and then with the sample fluid, onto the gratings, and reference and sample patterns are obtained thereby on the screen. The sample pattern will be different from the reference one if the optical power of the biconvex lens changes due to the change of the liquid in the cell. The difference between the reference pattern and the sample pattern is then measured and used for calculating the refraction index of the sample fluid.

EP 1324015 describes similar techniques for measuring optical parameters of a phase object based on recording a moiré pattern viewed through the phase object. The moiré pattern is formed by illuminating two gratings by diffuse light, and projecting their images on a screen through the phase object. The optical parameters of the phase object are calculated from the moiré pattern.

Such methods require relatively complex optical systems, recording and measurement of images and sophisticated calculations in order to determine accurately a change in the refraction index of the liquid.

Co-pending International Patent Application PCT/IL2003/000987 discloses, inter alia, methods systems and devices for identification of changes in fluids.

SUMMARY OF THE INVENTION

In accordance with the present invention, there is provided an optical indicator for identification of a changed state of a fluid with respect to a reference state of the same fluid, the fluid having an optical parameter changing with the change of the state of the fluid. The optical indicator is mountable to or integral with a container for the fluid. The indicator comprises:

a) a transparent enclosure including a wall and a cavity in fluid communication with the container;

b) an object observable through the enclosure c) an optical system having an optical axis and enabling observation of the object when illuminated by diffuse light, via the enclosure filled with the fluid.

The optical indicator is designed such that the object observed in the changed state of the fluid is optically distinctive from an image of the object observed in the reference state of the fluid due to a change of the optical parameter. At least one of the reference image and the changed image is predetermined, so that the identification can be performed by comparing a current image of the object to the predetermined image.

In a basic embodiment of the present invention, the optical parameter is the refraction index of the fluid, and the object is a pair of gratings disposed in planes spaced along the optical axis such that the observed image is a moiré pattern. Preferably, the planes of the gratings are parallel.

The gratings may be a pair of Ronchi rulings, preferably one set of Ronchi rulings being disposed at sharp angle with respect to a second set of Ronchi rulings. The gratings may also comprise curved lines, such as concentric circles, ellipses, etc., also in combination with Ronchi rulings.

Two pairs of such gratings may be used, each pair producing a moiré pattern such that the patterns can be observed superimposed or juxtaposed.

The wall of the enclosure is preferably formed as an optical lens or prism constituting part of the optical system. The cavity and the wall are formed such that when the cavity is filled with the fluid in the reference state, the transparent enclosure constitutes a lens or a prism with predetermined optical power, preferably zero optical power. In such case, the moiré pattern observed in the reference state of the fluid is an infinite fringe (no fringe). The fringe becomes observable when the fluid changes its state.

The optical system of the optical indicator may comprise a lens and a pinhole so as to project the image on the retina of an observer's eye. Alternatively, the optical system may comprise a compensating lens and an eye-piece lens.

In one embodiment of the present invention, the wall of the transparent enclosure is formed as two concavo-convex lenses with the cavity defined between convex sides of the lenses. Alternatively, the transparent enclosure may be formed with the cavity between concave sides of the lenses.

In another embodiment, the cavity is formed as a double-wedge prism with the gratings at wedges' bases and with walls formed as two triangular prisms adjacent to either side of the double-wedge prism. Alternatively, the wall of the transparent enclosure may be formed as a triangular prism with the cavity formed as two wedge prisms adjacent to either side of said triangular prism, the gratings being disposed at the wedge prisms' bases.

The optical indicator may be adapted for integral mounting in a closure of the container or in a pipe for transporting the fluid, or in a package of drinkable liquid or liquid medication.

The optical indicator is preferably made of plastic material such as polycarbonate or cyclic olefin copolymer. The indicator may be made of single molded piece of material and may be disposable.

In a specific embodiment of the present invention, the optical indicator further comprises a housing accommodating the enclosure and a transparent mask carrying the gratings and disposed transversely to the optical axis. The housing has a pinhole for observation of the moiré pattern.

The housing of the optical indicator may have a port for connecting to the container and providing the fluid communication to the cavity.

The optical indicator may be made integral with a cap of the container, the housing and the mask constituting portions of the cap.

Alternatively, the optical indicator may be made mountable in a transparent bottle with a neck, with the optical axis transverse to the neck.

The optical indicator may be integral with a portion of a pipeline or a fitting for transferring the fluid, such that at least part of the fluid passes through the cavity. For example, the container may be an infusion bag and the optical indicator may be integral with an injection port of the infusion bag.

In another basic embodiment, the optical parameter is the polarization angle of the fluid and the object is a polarization filter. A second polarization filter is included in the optical system, preferably with perpendicular direction of polarization. The observed image is either a dark field of view or bright field of view.

Identification of the polarization angle change may be combined with identification of refraction index change, in an optical indicator comprising both polarization filters and pairs of gratings.

The present invention makes use of the idea that small changes in optical parameters of some fluids may be indicative of changes in their composition, temperature and other non-optical properties. Thus, changes of non-optical properties may be monitored and detected by an optical indicator.

The present invention effectively uses qualitative comparison and identification of images instead of quantitative assessment or measurement. The former may be done by naked eye through quite simple, cheap and reliable optical indicators. Moreover, the identification may be done by a non-qualified observer such as a user of a fluid product, following simple instructions and exemplary patterns.

Contrary to methods of measurement, the designer of an optical indicator in accordance with the invention has previous knowledge of the optical parameter both in the reference state and in the changed state of the fluid, so that he can design the optical system of the indicator accordingly to make the changed state of the fluid highly distinguishable. Therefore, the indicator may be adjusted for easy identification of a small predetermined change of the optical parameter without measuring it.

Alternatively, the optical indicator may be used for verification, and/or authentication and/or detection purposes, as it may be used for indicating whether the fluid being tested has been tampered with or diluted or substituted by another fluid having different optical properties (such as, but not limited to, different refractive index or different rotation of the plane of polarized light).

The reference and/or the changed pattern may be made known to the observer for identification by verbal description, or may be depicted or described on the optical indicator or on the packaging. Alternatively, the reference pattern may be recorded in the optical indicator and be made visible therein simultaneously with the currently observed pattern, e.g. superimposed thereon for easier comparison.

The optical indicator of the present invention is miniature, simple, reliable and cheap in production. It may be manufactured by injection-molding from common polymers and may even be made disposable. The optical indicator may be used in a wide variety of applications pertinent to detection of changes in the state of liquids, gases, mixtures, suspensions and the like, such as production, storage, packaging and monitoring of chemicals, oil, medicines, food, drinks, water, etc.

BRIEF DESCRIPTION OF THE DRAWINGS

In order to understand the invention and to see how it may be carried out in practice, embodiments will now be described, by way of non-limiting examples only, with reference to the accompanying drawings, in which like components are labeled with like reference numerals.

DETAILED DESCRIPTION OF THE INVENTION

Figure 1:
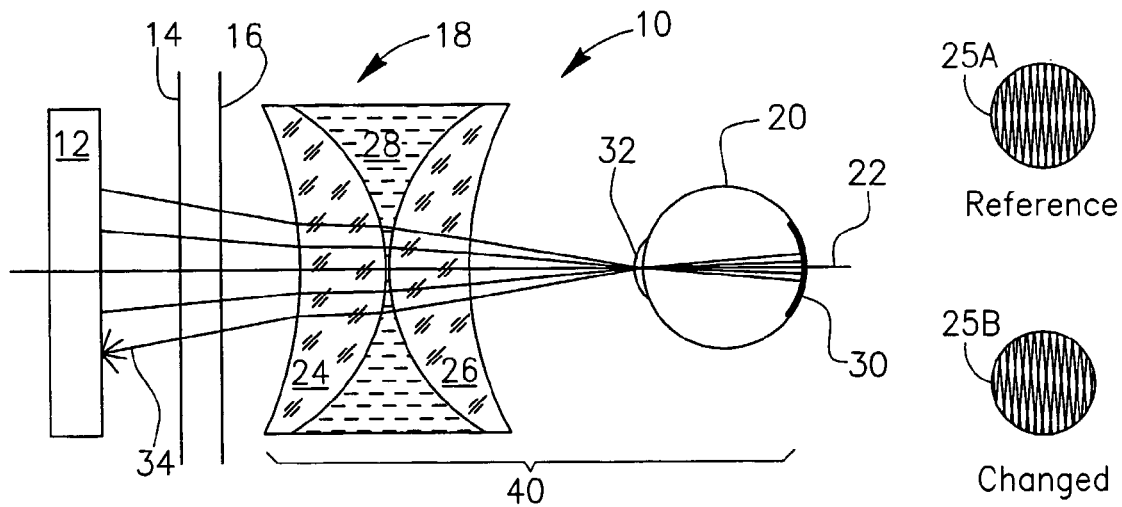
FIG. 1 is a schematic diagram illustrating an optical arrangement for identification of changes in the state of a fluid using an enclosure with biconcave cavity and concave-convex lenses in the wall.

With reference to FIG. 1, there is shown an exemplary optical arrangement 10 for an optical indicator in accordance with the present invention. The optical arrangement 10 comprises two gratings 14 and 16 that may be illuminated by ambient light or (optionally) by a light from a diffuse light source 12. The arrangement 10 further comprises a transparent enclosure 18 with an axis 22 coinciding with the direction of observation. The axis 22 passes through the gratings 14 and 16, the enclosure 18 and the eye 20 of the observer. The gratings 14 and 16 are substantially parallel gratings and are both generally perpendicular to the axis 22. However, it is noted that the gratings 14 and 16 need not obligatorily be parallel gratings and that some embodiments of the invention may use non-parallel gratings.

The light source 12 may be any common fluorescent or incandescent lamp with or without a diffuser (not shown), but any other suitable source for providing diffused light, may be used as is known in the art. The gratings 14 and 16 are common Ronchi rulings with a substantially identical period. It is noted that while the gratings 14 and 16 of FIG. 1 are implemented as common Ronchi rulings with a substantially identical period, the present invention may also be implemented with other types of gratings, including but not limited to diffractive gratings or any other type of suitable grating known in the art. It may also be possible to use grating pairs (diffractive type or, Ronchi ruling type or any other suitable other types of gratings) in which one grating has a grating period that is different than the grating period of the other grating of the grating pair.

The enclosure 18 is built of two concave-convex lenses 24 and 26, whose convex faces are almost touching. A cavity 28 defined between the lenses 24 and 26 is configured to be filled with a liquid to be monitored and/or checked and/or authenticated. The liquid may be any liquid whose state may change in time. The liquid's original state is considered to be a reference state, and it differs from the changed state by a known difference in the refraction index. The radii of curvature of the surfaces of the lenses 24 and 26 may be selected so as to minimize distortion of the image while keeping the overall optical power of the enclosure 18 when the enclosure 18 is filled with liquid in the reference state close to zero.

The usage of the two lenses 24 and 26 with convex faces almost touching each other, allows identification of changes in turbid or highly absorptive fluids because the fluid layer disposed between the convex faces of the lenses 24 and 26 may be made very thin and transparent.

The light source 12 emits light in all directions and illuminates the gratings 14 and 16 with diffuse light (the light source 12 may be the ambient light). The eye 20 projects images of the gratings 14 and 16 on the retina 30 where a moiré pattern is formed. The pupil 32 blocks some of the rays such that only a small portion 34 of the light reaches the retina 30.

The enclosure 18 and the eye 20 constitute an imaging system 40 focused on the space between the gratings 14 and 16. The eye 20 adjusts its focal length such that light rays passing through both of the gratings 14 and 16 are projected on the retina 30 simultaneously.

The size of each of the grating images on the retina is determined by the magnification of the imaging system 40, which in turn depends on the distance of the gratings 14 and 16 from the enclosure 18 and on the distance between the enclosure 18 and the retina 30 (the object and image distances, respectively). The gratings 14 and 16 have different positions along the optical axis 22. Therefore, the respective magnifications for the gratings 14 and 16 are different when the enclosure 18 has a non-zero optical power. The images of the gratings 14 and 16 projected on the retina 30 may thus have different periods which results in the formation of a moiré pattern (fringe), whose frequency or orientation depends on the actual magnification difference. In the particular example shown in FIG. 1, the two gratings 14 and 16 are rotated slightly relative to one another (around the axis 22), such that the orientation of the rulings or lines on the grating 14 are inclined at an angle to the rulings on the grating 16 within the plane of each grating (in other words, if the rulings or lines of the grating 14 are projected onto the plane of the rulings or lines of the grating 16, the projected lines or rulings of the grating 16 will be oriented at an angle to the lines or rulings of the grating 14. This inclination may improve the visual detectability of the resulting pattern) and the imaging system magnification defines the moiré fringe orientation.

The fluid or liquid disposed in the enclosure 18, in its reference state having a reference refraction index, is characterized by a reference moiré pattern with a predetermined frequency or orientation. The schematic diagram 25A of FIG. 1 illustrates a specific (non-limiting) example of a reference moiré pattern with a specific fringe orientation.

When the liquid being tested changes its state, it's refractive index changes. The optical power of the enclosure 18 in which the liquid is disposed changes accordingly, causing a change in the magnifications for the two gratings 14 and 16. The projected images of the gratings 14 and 16 on the retina 30 change and produce a changed moiré pattern that has a different fringe orientation from the reference moiré pattern. The schematic diagram 25B of FIG. 1 illustrates a specific (non-limiting) example of a moiré pattern resulting from a change in the refractive index of the fluid or liquid disposed within the enclosure 18 (or, alternatively, resulting from disposing in the enclosure 18 a different fluid or liquid having a refractive index different than the reference refractive index). The fringe orientation of diagram 25B is visibly or detectably different than the fringe orientation of the reference moiré pattern of diagram 25A. The observed fringes represented by the diagram 25B are visibly tilted with respect to the observed (or memorized) fringes in the reference moiré pattern represented by the diagram 25A.

Figure 2:
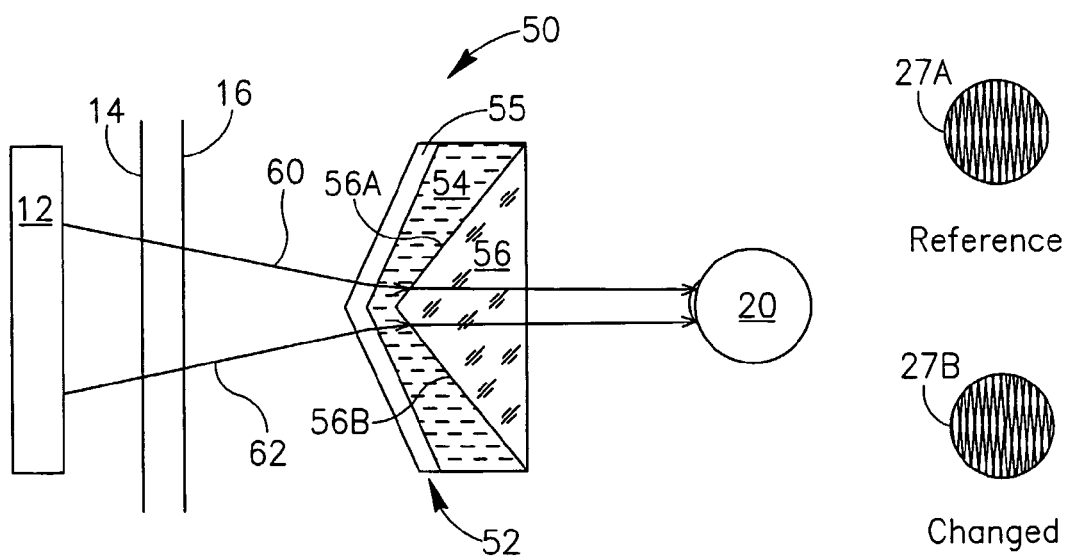
FIG. 2 is a schematic diagram illustrating an optical arrangement for identification of changes in the state of a fluid using an enclosure with bi-prismatic cavity and central prism in the wall.

With reference to FIG. 2, another exemplary optical arrangement 50 is shown, making use of a transparent prismatic enclosure 52. The prismatic enclosure 52 has a double-prism shaped cavity 54 formed therein and includes a first cavity wall 55 and a compensating prismatic wall 56. The optical arrangement 50 further includes two gratings 14 and 16. The gratings 14 and 16 are illuminated by ambient light or by light from a diffuse light source 12. The images of the gratings 14 and 16 and the fringe patterns formed therefrom may be observed by the eye 20. It is noted that the light source 12 is optional, as described hereinabove with reference to FIG. 1, and that the illumination of the gratings 14 and 16 may be implemented using available ambient light.

A first ray 60 of diffused light is shown as refracted in a first direction at the prism interface 56A. The fringe pattern in the first half of the enclosure 52 is thus shifted in a direction perpendicular to the fringe direction. The magnitude of the shift is proportional to the deflection angle that depends on the refractive index difference across the interface 56A. Similarly, a second ray 62 is refracted in a direction opposite from the direction of refraction of the ray 60 resulting in a fringe shift in a direction opposite to the shift in the first half of the enclosure 52. The eye 20 of a viewer observes a step (or a discontinuity) in the fringe pattern formed on the retina of the eye 20 by the two halves of the enclosure 52, as schematically illustrated in the diagram 27B of FIG. 2.

Preferably, (but not obligatorily) the compensating prismatic wall 56 is selected (by suitably selecting the refractive index of the material forming it) such that the observable step in the fringe pattern is zero (meaning that a step is not observed) when the fluid in the enclosure 52 is in the reference state and the fringe pattern will look continuous, as schematically illustrated in the diagram 27A of FIG. 2.

If the fluid disposed within the prismatic cavity 54 is in changed state, having different refraction index, or if a different fluid having a refraction index different than the reference refraction index is disposed within the prismatic cavity 54, the viewer will observe an interruption (observed as a step or a discontinuity) in the middle of the fringe pattern (See the schematic representation of the observed moiré patterns of diagram 27B of FIG. 2).

Figure 3:
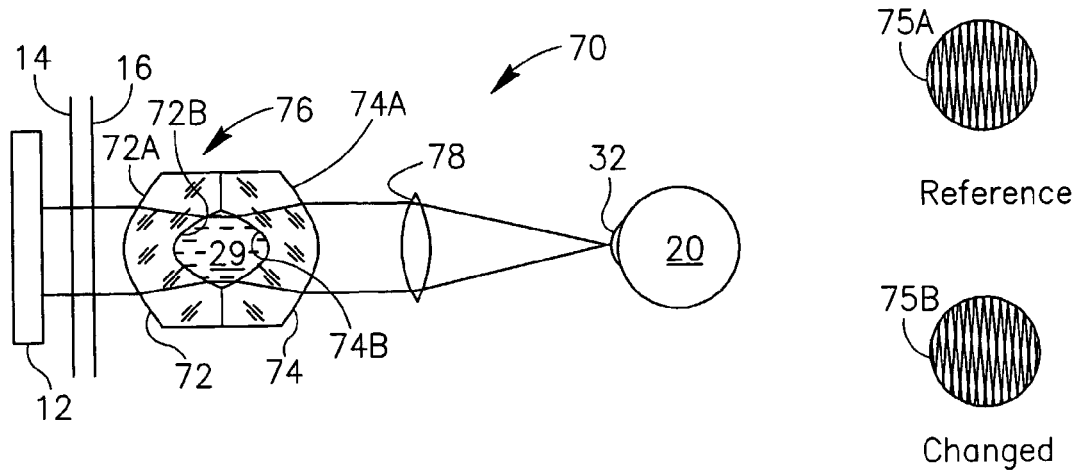
FIG. 3 is a schematic diagram illustrating an optical arrangement for identification of changes in the state of a fluid using an enclosure with biconvex cavity, aspheric lenses in the wall, and a collimating lens.

With reference to FIG. 3, a schematic optical arrangement 70 is illustrated, where aspherical lenses 72 and 74 are used as walls of a transparent enclosure 76. The light source 12 and the gratings 14, 16 are similar to the ones in the optical arrangements shown in FIGS. 1 and 2. The lenses 72 and 74 define therebetween a cavity 29. The cavity 29 may be an open cavity configured to be filled (completely or partially) with a fluid or liquid to be tested and/or monitored and/or authenticated. A collimator lens 78 focuses the image of the gratings onto the eye 20.

The aspheric surfaces 72A, 72B, 74A and 74B of the lenses 72 and 74 reduce spherical aberration, thus producing straight fringes or nearly straight fringes. This increases the domain of straight fringes over the entire aperture of the optical system. In the optical arrangement 70, differences between fringe orientations in the reference state of the fluid disposed in the cavity 29 and in the changed state appear more distinctive. For reasons similar to the reasons described in detail hereinabove for the optical arrangement 10 of FIG. 1, the visual appearance of the image observed by the eye 20 may change in appearance if the refractive index of the fluid disposed in the cavity 29 changes. Similarly, the refractive index of the material or materials from which the lenses 72 and 74 are made may be selected such that when a fluid having a predetermined refractive index is disposed within the cavity 29, the image observed by the eye 20 is represented by the schematic diagram 75A of FIG. 3.

If the fluid in the cavity 29 changes it's refractive index relative to the refractive index of the same fluid at the reference state, or if the fluid in the cavity 29 is replaced by a different fluid having a refractive index different than the refractive index of the reference fluid, the appearance of the image observed by the eye 20 may change as illustrated in the schematic diagram 75B of FIG. 3.

It is noted that, in the example illustrated in FIG. 3, both inner surfaces 72B and 74B and the outer surfaces 72A and 74A of the lenses 72 and 74, respectively are aspheric surfaces. However, in accordance to other embodiments of the present invention, some of the surfaces 72A, 72B, 74A and 74B of the lenses 72 and 74, respectively may be spherical surfaces and/or plane surfaces.

Figure 4:
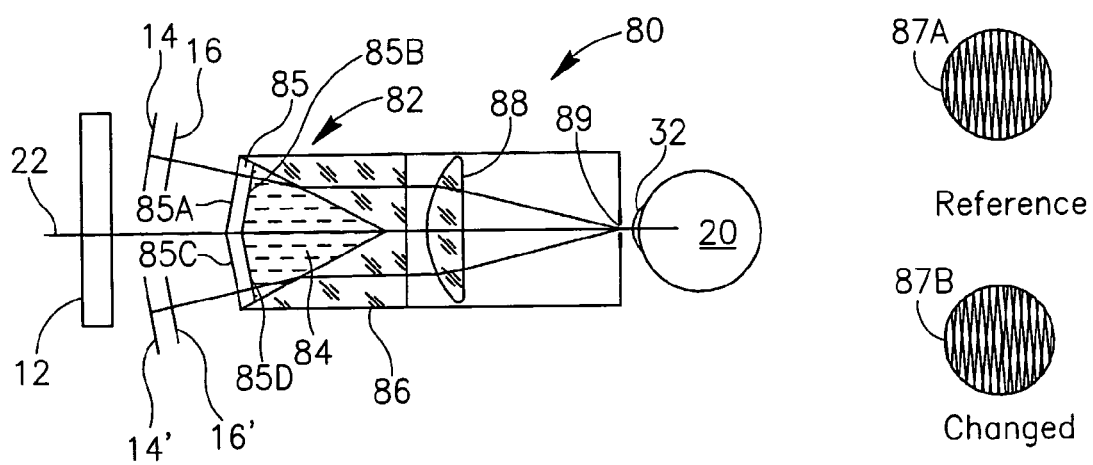
FIG. 4 is a schematic diagram illustrating an optical arrangement for identification of changes in the state of a fluid using an enclosure with double-wedge prism cavity, bi-prismatic wall and a collimating lens.

With reference to FIG. 4, a schematic optical arrangement 80 is illustrated, comprising an enclosure 82 having a double-wedge prism cavity 84 formed therein. The enclosure 82 includes a first cavity wall 85 and a bi-prismatic wall 86. The optical arrangement 80 further includes a collimating lens 88 and a pinhole 89. The optical arrangement 80 also includes the light source 12 and the gratings 14, 16 which are similar to the gratings illustrated in FIG. 1, however a second pair of gratings 14' and 16' is also included in the optical arrangement 80. Each pair of gratings is disposed opposite the base of one wedge of the double-wedge prism cavity 84 (as illustrated in FIG. 4). The two sets of rulings (not shown) in each pair of gratings of the two pairs of gratings are inclined at a small angle (not shown) to each other, as explained hereinabove in detail with reference to FIG. 1, so that each pair of gratings projects a moiré fringe in the eye 20. For example, the rulings of the grating 14 are inclined at a small angle relative to the rulings of the grating 16 and the rulings of the grating 14' are inclined at a small angle relative to the rulings of the grating 16'.

The optical arrangement 80 may be manufactured and configured taking into account the known refractive index of reference fluid or liquid, such that the two fringes (one fringe formed by the pair of gratings 14 and 16 and the other fringe formed by the pair of gratings 14' and 16') are continuous when the fluid in the cavity 84 is in the reference state. The schematic diagram 87A of FIG. 4 schematically illustrates the view of an exemplary continuous fringe observed by the eye 20 when the fluid disposed within the cavity 84 is the reference fluid in the reference state.

When the fluid in the cavity 84 changes its refraction index, or when the fluid in the cavity 84 is tampered with or diluted resulting in a change its refractive index, or is replaced with another fluid having a different refraction index, the two fringes are shifted in opposite directions. The shift or discontinuity of the two fringes is readily visible by naked eye. The schematic diagram 87B of FIG. 4 schematically illustrates the view of a discontinuous fringe observed by the eye 20 when the fluid disposed within the cavity 84 changes its refractive index or is tampered with or diluted resulting in a change its refractive index or replaced with another fluid having a different refraction index.

Figure 5A:
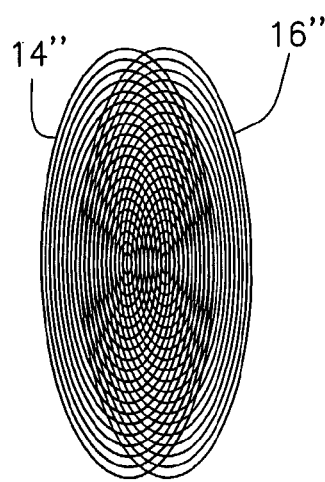
FIGS. 5A, 5B and 5C are schematic diagrams illustrating gratings comprising concentric circles, and moiré patterns from such gratings visible in the changed state of the fluid, by means of an optical indicator in accordance with the present invention.
Figure 5B:
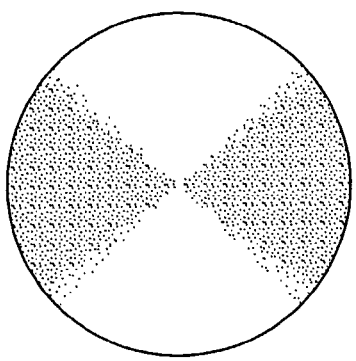
Figure 5C:
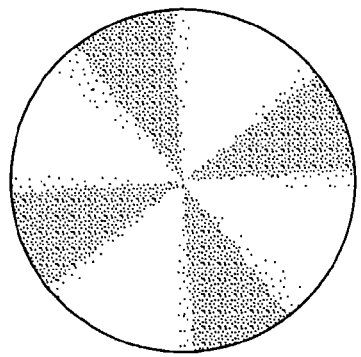

The gratings of the optical devices of present invention may also comprise curved lines or rulings, such as concentric circles. Reference is now made to FIGS. 5A-5C. FIG. 5A is a schematic diagram illustrating a perspective view of a pair of gratings 14" and 16" having concentric circular lines (or rulings) usable in the present invention. It is noted that, for the sake of clarity of illustration, only the lines of the gratings are shown in FIG. 5A. The reference image (not shown) may be a zero-fringe with no moiré pattern visible, while the changed observed image may comprise two hyperbolic sectors (as is illustrated in FIG. 5B) or four hyperbolic sectors (as is illustrated in FIG. 5C) or another larger number of hyperbolic sectors depending, inter alia, on the type and arrangement of the gratings 14" and 16", and the change in the refractive index of the checked fluid.

It is noted that, in accordance with one aspect of the present invention, it is possible to use pairs of complementary inverse gratings (gratings in which the transparent lines of one grating are where the opaque or non-transparent lines are in the second complementary grating) to obtain a "zero-fringe" configuration in which most or all of the image observed by the user is a dark image (with no fringes visible) by arranging the transparent lines of the first grating to be directly opposite the opaque lines of the second grating of the pair, because the light passing through the transparent lines of the first grating is substantially blocked by the opposed opaque lines of the second grating.

Alternatively if each transparent line (or region) in the first grating is directly facing a transparent line of the second grating, the "zero-fringe" image observed will be a lighter image with substantially no fringes because the light passes through the opposing transparent lines (or regions) of both gratings of the pair.

It is noted that while the lines or rulings of the gratings 14" and 16" are patterned as concentric circles, other curved forms may also be used, such as but not limited to, ellipsoidal lines or rulings, parabolic lines or rulings or any other suitable types of curved lines or rulings.

It is noted that the gratings usable with the present invention are not limited to the exemplary gratings shown hereinabove and illustrated in the drawing Figures. Many other types of gratings with different ruling or line configurations may be used in implementing the present invention, as is known in the art. Accordingly, the observed (or detected, if a detector is used instead of an eye) reference image and the changed image may be different than the exemplary observed (or detected) reference and changed images illustrated in the drawings.

More examples of moiré patterns obtainable by superposition of two gratings can be found in Olof Bryngdahl, BEAT PATTERN SELECTION—MULTICOLOR GRATING MODE, *Optics Communications*, vol. 39/3, pp. 127-131 (1981); ORTHOGONAL STATES GRATING MODE, ibid., vol. 41/4, pp. 249-254 (1982); and MOIRÉ ANALYSIS OF STRAIN, A. J. Durelli, V. J. Parks, Prentice Hall, N.J. 1970, incorporated herein by reference in their entirety.

Figure 6A:
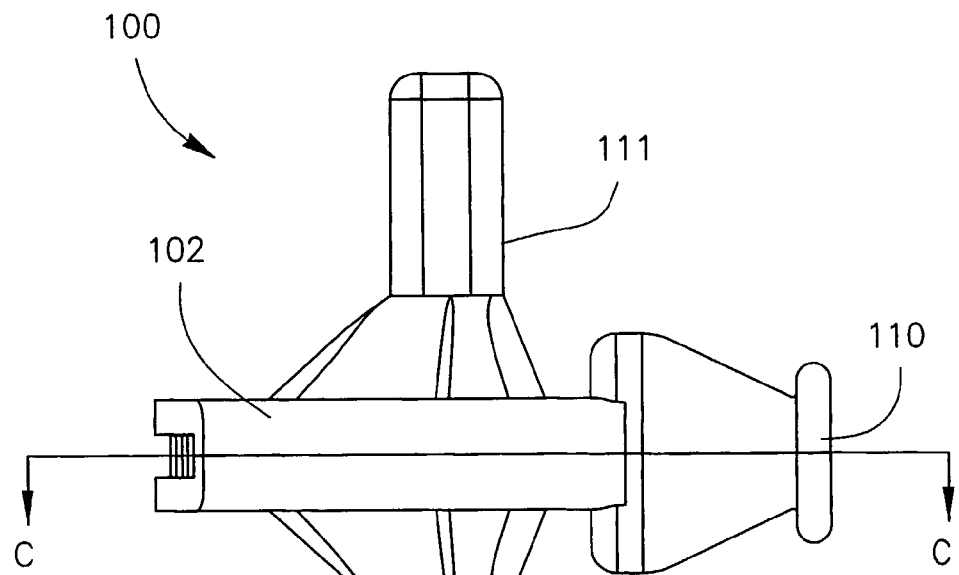
FIGS. 6A, and 6C which are a schematic isometric view, and cross-sectional view, respectively, illustrating a flowthrough optical indicator connectable to an infusion system and having a fluid inlet and a fluid outlet, in accordance with an embodiment of the present invention.
Figure 6B:
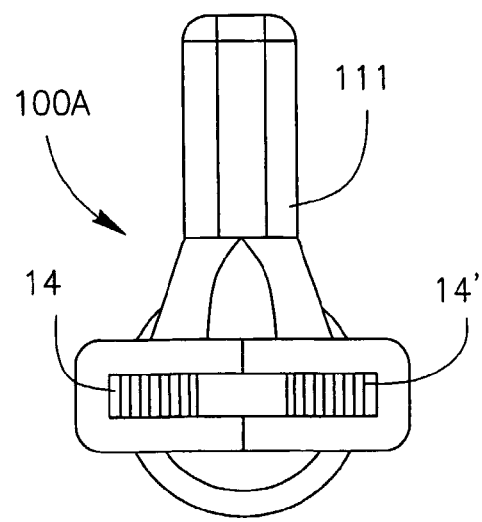
FIG. 6B is a schematic side view illustrating an optical indicator connectable to an infusion system and having a single fluid inlet port, in accordance another embodiment of the present invention.
Figure 6C:
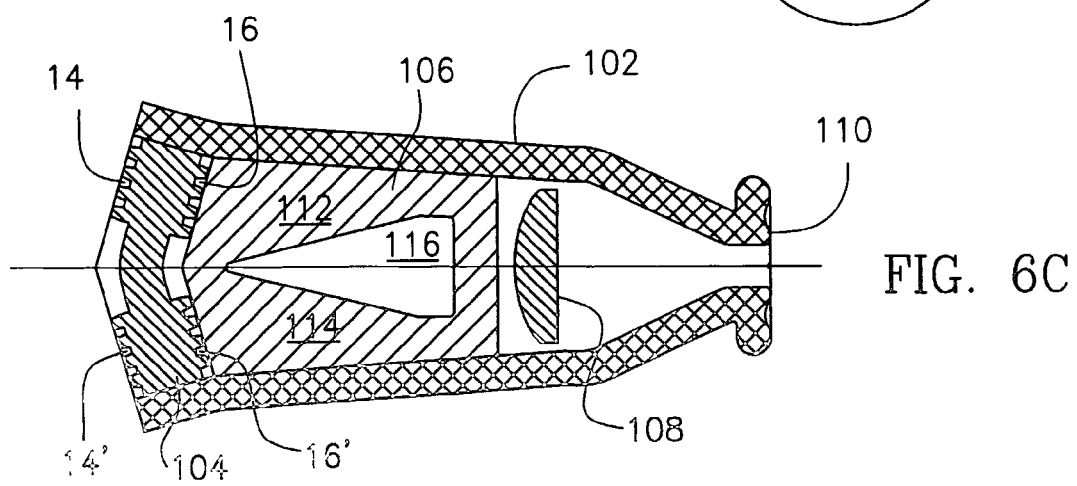

Reference is now made to FIGS. 6A, and 6C which are a schematic isometric view, and cross-sectional view, respectively, illustrating a flow-through optical indicator connectable to an infusion system and having a fluid inlet and a fluid outlet, in accordance with an embodiment of the present invention.

The optical indicator 100 comprises a housing 102, a mask 104, a transparent enclosure 106 and a collimating lens 108. The housing 102 has a pinhole 110 for the observer's eye 20, and an inlet tube 111 for letting the monitored liquid into the optical indicator 100. The mask 104 has two pairs of gratings 14, 16 and 14', 16' at its inner and outer surface, respectively. The enclosure 106 is formed with two prismatic walls 112 and 114 and a prismatic cavity 116 between them. The cavity 116 is in fluid communication with the inlet tube 111.

An outlet tube 118 is in fluid communication with the cavity 116. Using the outlet tube 118, the optical indicator 100 may be connected directly into a pipe or a flexible conduit or tube and the liquid entering through the inlet tube 111 and flowing into the cavity 116 may flow out through the outlet tube 118.

Reference is now made to FIG. 6B which is a schematic side view illustrating an optical indicator connectable to an infusion system and having a single fluid inlet port, in accordance another embodiment of the present invention. The optical indicator 100A is similar to the optical indicator 100 of FIGS. 6A and 6C except that it does not include the outlet tube 118 of the optical indicator 100 and is therefore not configured as a flow-through indicator. In the optical indicator 100A, the fluid may enter the cavity 116 of the enclosure 106 through the inlet port 111, and may possibly be made to exit the cavity 116 through the same inlet tube 111 by inverting the optical assembly 100A upside-down.

Figure 7A:
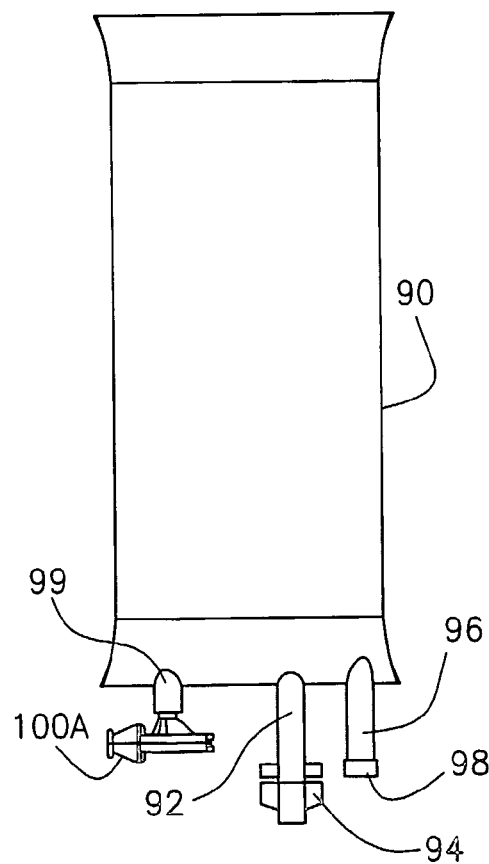
FIGS. 7A and 7B are schematic views of an infusion system with the optical indicator of FIGS. 6A and 6C connected thereto.
Figure 7B:
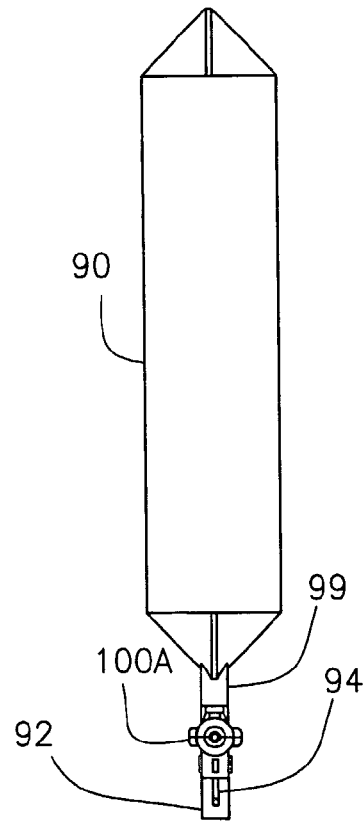

Infusion systems are used for direct introduction of medication into the veins of a patient. With reference to FIGS. 7A and 7B, a typical infusion system comprises a bag 90 with physiological solution comprising, inter alia, NaCl with predetermined concentration which has to be observed closely. The refraction index of the solution changes with concentration changes of the physiological solution. The bag 90 has an outlet port 92 with a stop valve 94 for connection to a dripper pipe, and an injection port 96 with a latex stopper 98 for injection of medicines into the solution contained in the bag 90. The optical indicator 100A is connected to a third port 99 by its inlet tube 111.

It is noted that the optical indicator 100 (of FIG. 6A) may be connected to the infusion system in a flow-through configuration, by suitably connecting the inlet tube 111 to the stop valve 94 of the bag 90 and by connecting a dripper pipe (not shown) to the outlet tube 118 of the optical indicator 100 (this configuration is not shown in FIGS. 7A and 7B, for the sake of clarity of illustration).

Each grating is a set of parallel Ronchi rulings that are disposed at a small angle to the rulings of the other set in the same pair (with respect to rotation around the optical axis), as described with reference to FIG. 4. The rulings on the mask 104 are formed as a phase grid but may be also printed, etc. The angles of the prisms are selected such that when the cavity 116 is filled with liquid in the reference state, the moiré fringes projected in the eye from each pair of gratings are parallel and continuous, as shown, for example, in diagram 87A of FIG. 4. When the liquid in the cavity 116 changes its refractive index, the two fringes are shifted in opposite directions, as shown, for example, in schematic diagram 87B of FIG. 4. It will be appreciated that the operation of the optical indicator 100 is similar to the operation of the optical arrangement 80 disclosed hereinabove and illustrated in FIG. 4.

It is noted that the use of the optical indicator with the infusion sets as disclosed hereinabove, is advantageous, as it enables the detection of changes in an optical property of the solution included within the infusion set, and may assist the prevention or avoidance of use of suspected or anomalous infusion sets, which may increase patient safety.

Figure 8:
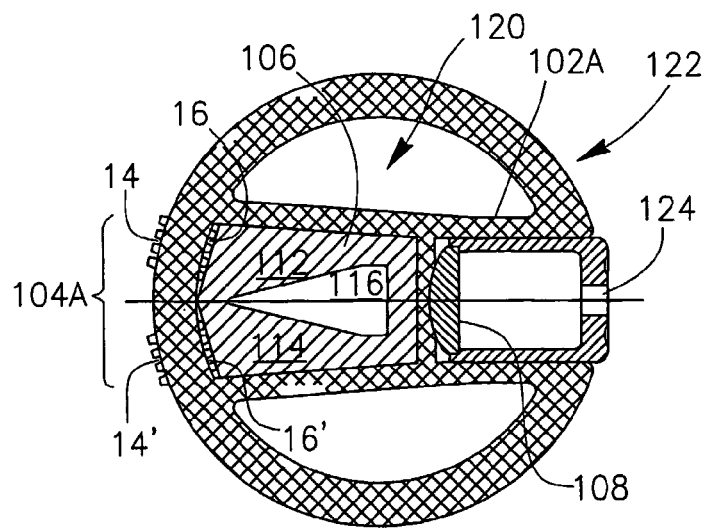
FIG. 8 is a schematic cross-sectional view illustrating an optical indicator integrated within a liquid container cap, using the optical scheme shown in FIG. 6C.

Reference is now made to FIG. 8 which is a schematic cross-sectional view illustrating an optical indicator integrated within a liquid container cap, using the optical scheme shown in FIG. 6C. The optical indicator 120 may be integrated into an injection-molded plastic cap 122 of a liquid container (the container is not shown). The optical indicator 120 has basically an optical configuration similar the configuration of the optical indicator 100, however the housing 102A, the mask 104A and the eyepiece 124 are formed as parts of the cap 122 or as parts attached thereto. The collimating lens 108 and the transparent enclosure 106 may be inserted in the injection mold during the manufacture of the cap. A similar indicator may be inserted in a bottle's neck (not shown) or may also be suitably integrated into or formed within any other suitable part of any fluid or liquid container known in the art.

It is noted that while the specific configuration of the optical indicator 120 is adapted for being conveniently integrated into an injection molded plastic cap 122 of a liquid container, It will be appreciated by those skilled in the art that the optical indicators of the present invention may be suitably integrated into or inserted into or attached to any other type of cap or container closure, or the like, using any type of attaching or integrating or forming methods known in the art. For example, the optical indicator may be separately manufactured or assembled using any suitable method known in the art and then inserted into or attached to or screwed into or glued within any suitably formed cap or container closure means known in the art. The specific example shown in FIG. 8 is given by way of example only and is not intended to be limiting in any way.

Figures 9A, 9B:
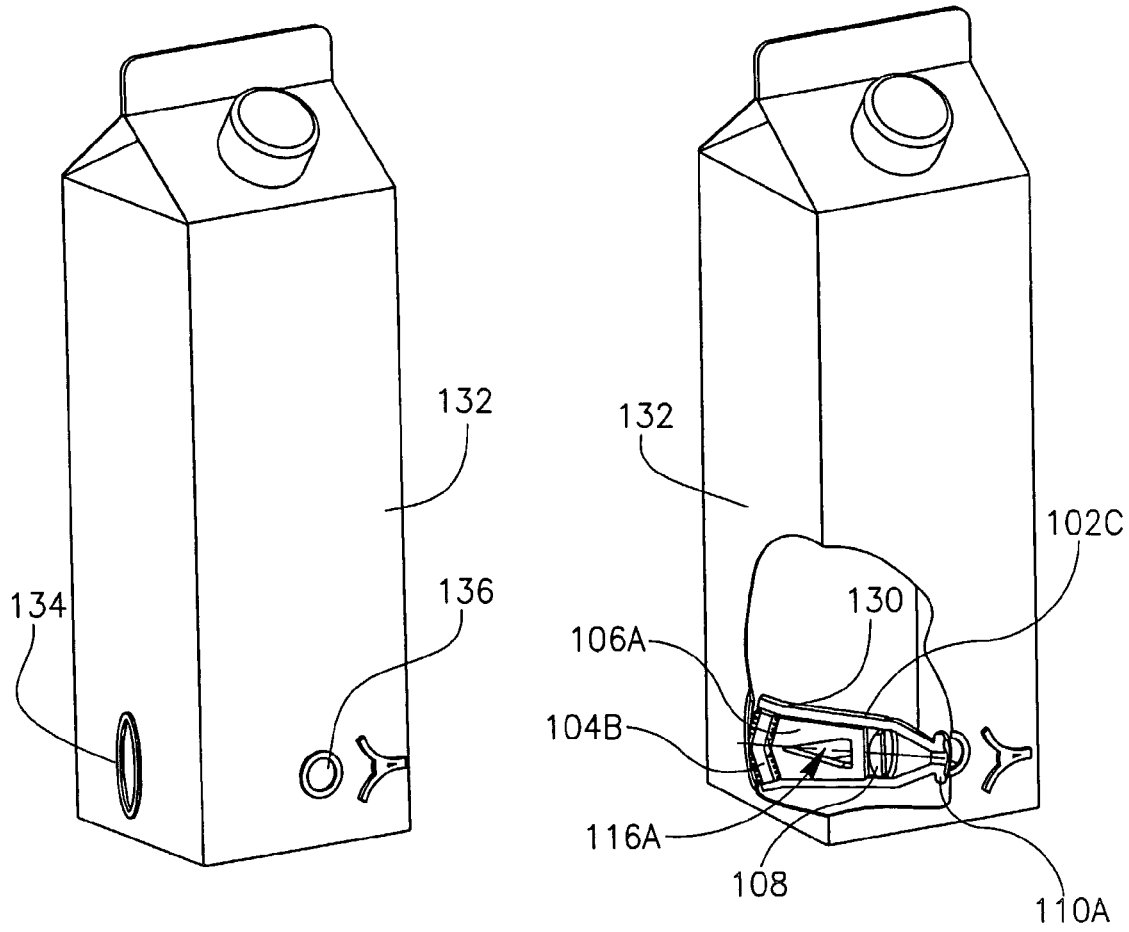
FIGS. 9A and 9B are schematic isometric and part isometric part cutaway views, respectively, illustrating an optical indicator integrated within a tetrapack milk box in accordance with an embodiment of the present invention.

Reference is now made to FIGS. 9A and 9B which are schematic isometric and part isometric part cutaway views, respectively, illustrating an optical indicator integrated within a tetrapack milk box in accordance with an embodiment of the present invention. The optical indicator 130 is built into a tetrapack milk bottle 132. The tetrapack bottle 132 has two transparent windows 134 and 136. The window 134 is for allowing the entry of the ambient light into the indicator 130, and the window 136 is for visual observation by as user. The indicator 130 is attached or mounted between the windows 134 and 136. The indicator 130 allows detecting changes in milk acidity through the changed refraction index of the milk.

The indicator 130 is of the bi-prismatic type having a housing 102C, a bi-prismatic transparent enclosure 106A, a mask 104B similar to the masks 104 and 104A (of FIGS. 6C and 8, respectively), and a collimating lens 108. The cavity 116A of the enclosure 106A is open on both sides to allow milk to fill the cavity 116A.

The optical assembly 130 is configured such that the reference liquid is fresh milk. When the milk in the bottle 132 is fresh and a user looks through the window 106 while directing the window 134 towards a source of diffused light (which may be the ambient light in the room) the user may see a reference pattern (such as, for example, the reference pattern 87A of FIG. 4).

When the milk disposed in the tetrapack bottle 132 changes its acidity (becomes sour), the refractive index of the milk changes and the form of the moiré fringe that may be observed through the window 136 changes in a visibly detectable manner as disclosed in detail hereinabove. For example, the moiré fringe image observed by the user may be as shown in diagram 87B of FIG. 4. The detectable difference in the observed moiré pattern indicates that the milk has become sour.

Figure 10:
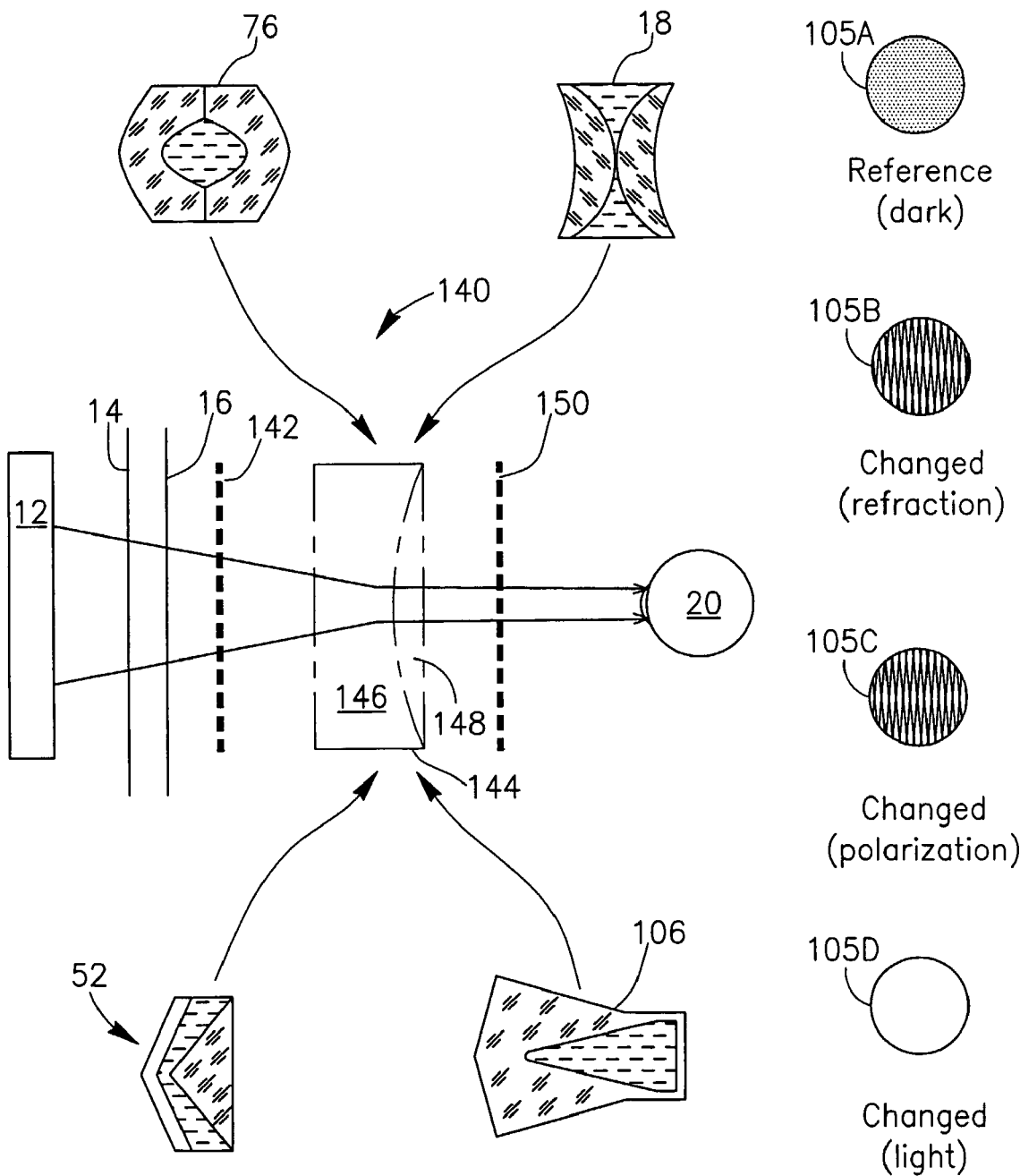
FIG. 10 is a schematic illustration of a general optical arrangement useful, inter alia, for detection and/or monitoring of changes in the polarization angle and/or the refraction index of a fluid or a liquid.

Reference is now made to FIG. 10 which is a schematic illustration of a general optical arrangement useful, inter alia, for detection and/or monitoring of changes in the polarization angle and/or the refraction index of a fluid or a liquid or a solution.

The optical arrangement 140 is configured for using the property of some solutions to rotate the angle of the plane of polarized light, where the angle of rotation depends on the concentration of the solute in the solution, with or without change in the refraction index of the solution. The arrangement 140 comprises a source of diffuse light 12, two gratings 14 and 16, a first polarizer 142, an enclosure 144 for the monitored solution with a cavity 146 and a compensating optical element 148, a second polarizer 150 and the eye 20 of the observer.

The enclosure 144 is only schematically shown as it may be constructed similar to any of the enclosures 18, 52, 76, 82 or 106 shown in the previous figures. The enclosure is designed to produce overall small optical power or prismatic deflection when filled with a fluid in a reference state. The cavity 146 may be in the form of a spherical lens, cylindrical lens, a prism, or the like, as described hereinabove and illustrated in the previous figures. The compensating optical element 148 is designed accordingly.

The polarizers 142 and 150 may be mounted or positioned within the arrangement 140, such that their respective planes of polarization of light are perpendicular to each other or are rotated at a predetermined angle to each other, depending on the reference angle of polarization and the change that must be detected.

It is noted that the angle of rotation of the plane polarized light by an optically active solute in a solution depends, inter alia, on the concentration of the optically active solute or component (or the density of the pure liquid if the pure liquid itself is optically active), on the distance through which the light travels (which may vary in accordance with the specific type and dimensions of the cavity used in the device), on the wavelength of the light used, on the temperature, on the solvent type (in a solution) and on the specific rotation of the optically active material in the solution or liquid. Most or all of these parameters may have to be taken into account when adapting the optical arrangement 140 for use with a specific reference liquid or reference solution.

Using the arrangement 140, specifically with the optical lens enclosures like 18 or 76, perpendicular polarization filters 142 and 150, and gratings 14 and 16 at small angle, an observer will see, for example:

a dark field of view if the solution does not rotate the plane of polarization (reference state);

a moiré pattern with horizontal fringes (changed polarization plane);

a moiré pattern with inclined fringes (changed polarization plane and changed refraction index).

It will be appreciated that, in accordance with an embodiment of the present invention, the arrangement 140 may be used without the gratings 14 and 16, for detection of changes in the angle of polarization only. In such a case, the observer may see, for example, a dark field of view in the reference state and a lighter field of view in the changed state. However, the arrangement 140 when used without gratings 14 and 16 may also be designed such that the observer may see, for example, a light field of view in the reference state and a darker field of view in the changed state.

Figure 11A:
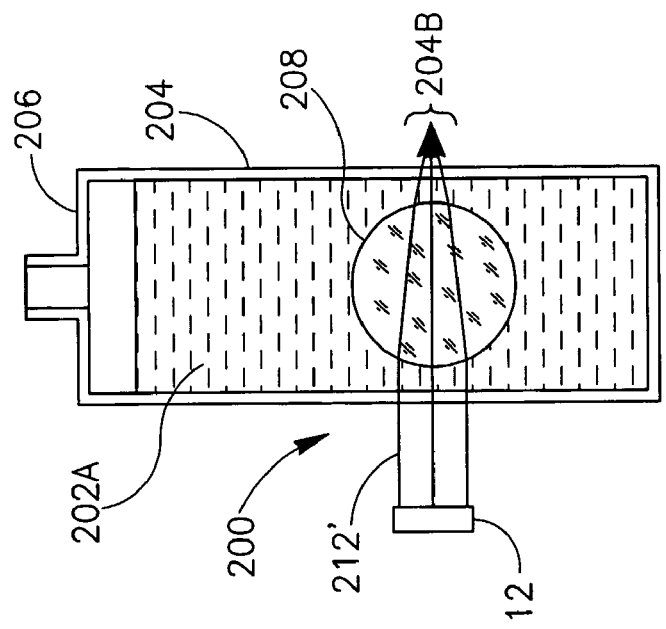
FIGS. 11A and 11B are a schematic cross-sectional diagrams illustrating an optical arrangement for detecting and/or monitoring a change in an optical property of a liquid in a container and/or for detecting tampering with a fluid in the container, in accordance with another embodiment of the present invention.
Figure 11B:
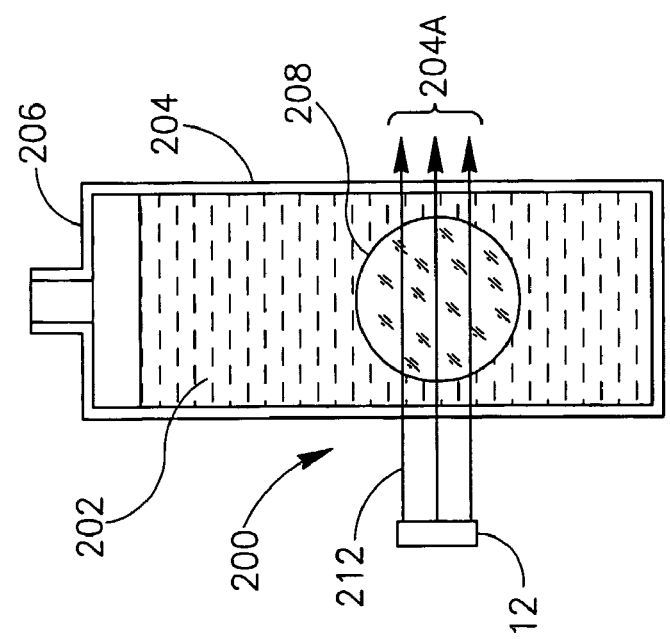

Reference is now made to FIGS. 11A and 11B which are a schematic cross-sectional diagrams illustrating an optical arrangement 200 for detecting and/or monitoring a change in an optical property of a liquid in a container or vessel and/or for detecting tampering with a fluid in the container, in accordance with another embodiment of the present invention.

The container 206 may be any suitable container or bottle or packaging or vessel that may hold or contain a liquid 202 therewithin. The walls 204 of the container 206 may be typically made of a material transparent to the wavelengths of light used for testing (such as, ambient light, visible light infrared light, ultraviolet light, broadband light, monochromatic light, or any other type of light or suitable electromagnetic radiation). It is noted that the walls 204 need not be entirely transparent but may be transparent only in selected portions thereof (not shown).

The optical arrangement 200 may include an optional light source 12 as disclosed in detail hereinabove. However, ambient light may also be used, as disclosed in detail hereinabove for other embodiments of the present invention.

The optical arrangement 200 also includes a transparent optical element disposed within the container 206. In the particular specific embodiment illustrated in FIG. 11A, the optical element is implemented as a transparent sphere 208. The sphere 208 may be made from any suitable transparent material such as, but not limited to, glass, plastic, a suitable polymer based material and the like.

Turning to FIG. 11A, in accordance with a an embodiment of the present invention, the refractive index of the material from which the sphere 208 is made may be selected for being identical (or substantially similar) to the refractive index of the reference liquid 202. For example, if the reference liquid 202 is a perfume, the sphere 202 may be made from a plastic material (or from any other suitable transparent material) having a refractive index identical or very close to the refractive index of the perfume.

Light rays 212 entering the container 206 pass through the sphere 208 and are projected as a diffuse large spot of light on a portion of the wall 204. Schematic diagram 210A illustrates an exemplary simulated image representative of the size and intensity of a spot of light that may be observed by an observer looking at the region 204A of the wall 204 when the reference liquid is in the container 206 and is in it's reference state.

Turning to FIG. 11B, the liquid 202 of FIG. 11A is replaced by a liquid 202A (as illustrated in FIG. 11B) which has an index of refraction different than that of the liquid 202. For example, if the liquid 202A is a non-authentic perfume or a fake perfume, or is a diluted version of the authentic reference perfume 202. Light rays 212' entering the container 206 pass through the sphere 208 and are refracted twice at the two interfaces between the liquid 202A and the sphere 208. The sphere 208 acts like a spherical lens and focuses the beams of light and projects them as a more intense smaller spot of light on a portion of the wall 204. Schematic diagram 210B illustrates an exemplary simulated image representative of the size and intensity of the spot of light that may be observed by an observer looking at the region 204B of the wall 204 when the liquid 202A in the container 206 is different than the reference liquid 202 and has a different refraction index than the reference refraction index. The resulting spot of light is smaller in comparison to the spot of light illustrated in the diagram 210A (of FIG. 11A) and has a substantially higher intensity due to the focusing effect.

Thus, the different appearance of the spot of light on the wall 204 of the container 206 may be used, for example, as an indicator that enables the observer to detect whether the perfume or liquid 202 in the container 206 has been tampered with or diluted or replaced by another non-authentic perfume.

Similarly, the appearance of the spot of light may be used to detect a change in the optical properties, such as, for example, a change in the refractive index of the liquid within the container 206 which may indicate a change in the liquid stored in the container 206. The liquid 202 in the container may be or beverage, such as but not limited to, hard liquor, cognac, whiskey or any other expensive or rare drink that may be tampered with or diluted or replaced with a different, cheaper or fake product.

It is noted that the container 206 need not be limited to the shape, geometry, or dimensions illustrated in FIGS. 11A and 11B. Rather, any suitable type of container or vessel may be used and many variations may be made to the shape or dimensions of the container 206, depending, inter alia, on the specific application. Similarly, the shape, size, refractive index, position within the container 206, distance from the walls 204 of the container 206 and degree of transparency of the optical element included in the optical arrangement 200 (of FIG. 11A and 11B), such as but not limited to the sphere 208, may be varied or modified depending on the particular application.

For example, the sphere 208 may be replaced with a lens shaped optical element (not shown) or by any other suitably shaped optical element known in the art that may operate in conjunction with the container 206 and the liquid included therein to function as a detector for the change of the refractive index of the liquid 202.

The optical element contained within the container 206 of the optical arrangement 200, such as but not limited to the sphere 208 may be implemented such that the visually observable change in the size and intensity of the light spot formed on the walls 204 of the container 206 will not be substantially affected by a change in the position of the sphere 208 or of any other optical element used relative to the walls 204.

Figure 12:
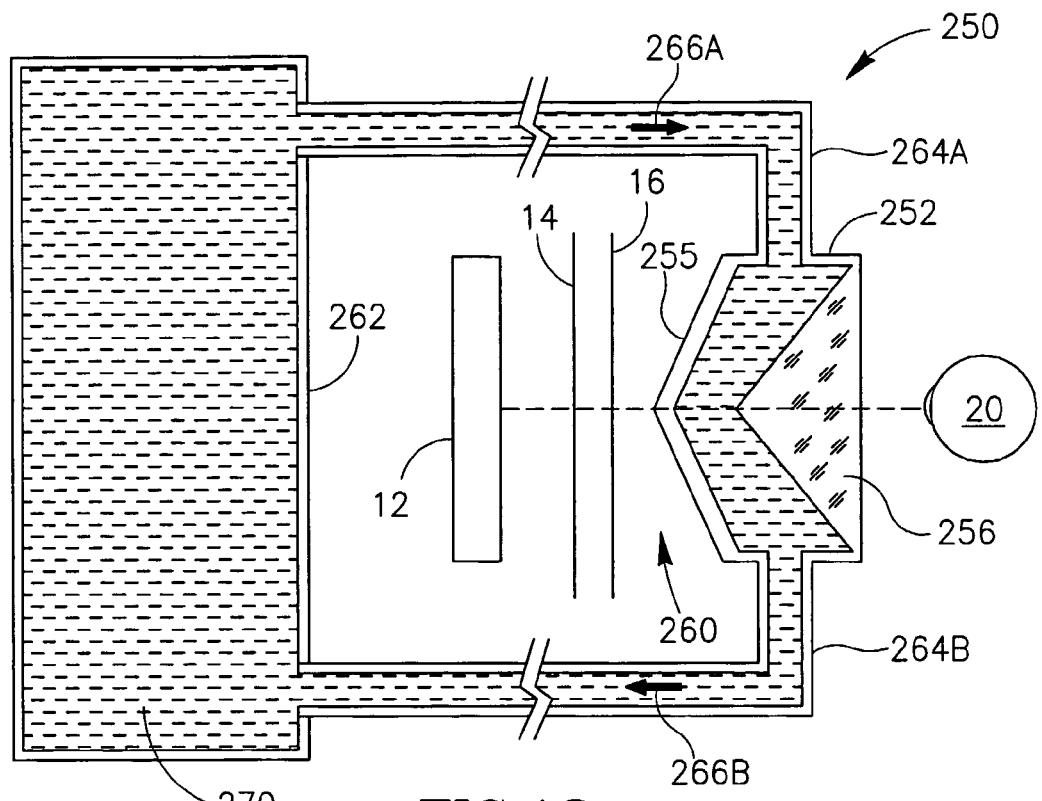
FIG. 12 is a schematic cross-sectional diagram illustrating an optical arrangement integrated into a fluid flow system and useful for detecting and/or monitoring a change in a fluid or a difference between a tested fluid and a reference fluid, in accordance with another embodiment of the present invention.

Reference is now made to FIG. 12 which is a schematic cross-sectional diagram illustrating an optical arrangement integrated into a fluid flow system useful for detecting and/or monitoring a change in a fluid or a difference between a tested fluid and a reference fluid, in accordance with yet another embodiment of the present invention.

The fluid flow system 250 is a fluid flow system having an optical arrangement 260 for detecting a change in the optical properties of a fluid flowing in the fluid flow system 250. The system 250 includes a fluid container 262 having a fluid 270 therein. The optical arrangement 260 includes a prismatic enclosure 252, an (optional) light source 12, and two gratings 14 and 16. The prismatic enclosure 252 has a double-prism shaped cavity 254 formed therein and includes a first cavity wall 255 and a compensating prismatic wall 256. The gratings 14 and 16 may be parallel gratings and the rulings or lines of the grating 14 may be inclined at a small angle to the rulings or lines of the grating 16 to enhance the visibility of the image produced when the fluid 270 changes its state or optical property or properties as explained in detail hereinabove for the optical arrangement 50 of FIG. 2.

The cavity 254 of the prismatic enclosure 252 is in fluid communication with the fluid container 262 through a fluid inlet conduit 264A and a fluid exit conduit 264B that are suitably connected to the prismatic enclosure 252.

The fluid (a liquid or a gas) 270 may be circulated in the system 250 by suitably moving or pumping the fluid 270 in the direction represented by the arrows 266A and 266B, such that it may continuously flow through the cavity 254. Various means for circulating the fluid 270 may be used such as suitable pump(s) (not shown), or gravity feeding arrangement, or any other pumping or fluid mobilization means or systems known in the art.

The operation of the optical arrangement 260 is as disclosed in detail hereinabove for the optical arrangement 50 of FIG. 2. It is noted that the light source 12 is optional and that the system 250 may be operated by using available ambient diffused light. It is also noted that the fluid container 262 may be any type of fluid container or vessel known in the art, such as, but not limited to a storage container or vessel, a reactor for reacting any fluid reaction mixture, a bioreactor, a fluidized bed reactor and the like. It is further noted that the specific optical arrangement 250 used of the system 250 is not obligatory and that all the other types of optical arrangements (such as, but not limited to the optical arrangements 40, 70, 80, or the optical indicator 100 as disclosed herein and/or any suitable variations thereof may be used in the system 250 with suitable adaptations instead of the optical arrangement 250 illustrated in FIG. 12)

The system 250 may be used in a variety of applications, such but not limited to, checking for changes in the properties of a fluid in a fluid storage container, monitoring for certain changes in the optical properties of a fluid such as a fluid reaction mixture to detect and monitor changes and/or to determine if a desired end-point has been reached in a reactor or a container (indicating that the reaction has advanced to a desired product concentration, or the like).

In another example, when a fluid such as a drink or beverage or a liquid food product wine, beer, milk, whiskey or the like is stored for extended time periods in a storage container, the optical arrangement included in of the system 250 (such as, but not limited to the optical arrangements 40, 70, 80, or the optical indicator 100 as disclosed herein and/or any suitable variations thereof) may be useful in detecting any change in one or more the optical properties of the fluid or product stored in the container 262. Detectable changes may include but are not limited to desirable or undesirable changes, such as, for example, the souring of milk, a fermentation end-point or a fermentation stage for wine and beer, the turning of wine to vinegar, or the like.

If the container 262 is used for storage of a perishable chemical or raw material in a fluid form, the optical arrangement used with the system 250 may allow detection of changes in the state of the chemical or raw material, such as, but not limited to, oxidation of the chemical, moisture content changes (which may be useful when the fluid 270 is a hygroscopic liquid), polymerization of the fluid 270, or the like.

It is noted that the systems and devices disclosed hereinabove and illustrated in the drawings are specific examples given in order to facilitate understanding of the principles of operation of the invention and are not intended to limit the scope of the invention to the specific embodiments shown. While the many embodiments of the present invention are configured for being used by a user or observer who may visually detect the image changes caused by the state change in the fluid being tested or monitored, the systems methods and devices of the present invention are not limited to visual observation of the pattern change. Rather the systems and devices of the present invention may also include a suitable detecting unit or detector device, such as but not limited to any photo-detector known in the art, or a suitable imager (such as but not limited to a CCD imager or a CMOS active pixel imager, or a camera or a video imager) Such photo-detector or imager may provide a suitable signal upon detecting a change in the light pattern produced by the specific optical arrangement or optical assembly used for detecting changes in the optical properties of the fluid being checked or monitored.

Figure 13:
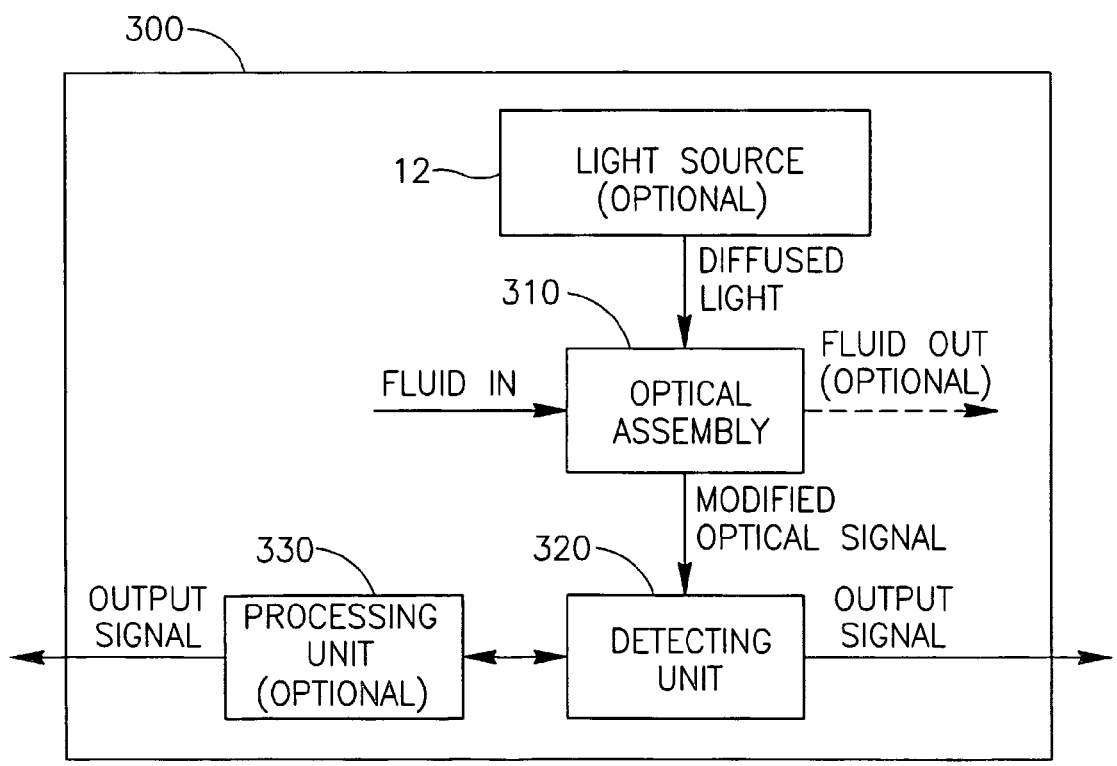
FIG. 13 is a schematic functional block diagram illustrating a general system having an optical arrangement for detecting and/or monitoring a change in a fluid or a difference between a tested fluid and a reference fluid, in accordance with another embodiment of the present invention.

Reference is now made to FIG. 13 which is a schematic functional block diagram illustrating a general system having an optical arrangement useful for optically detecting and/or monitoring a change in a fluid or a difference between a tested fluid and a reference fluid, yet another embodiment of the present invention.

The system 300 includes an optical assembly 310. The optical assembly 310 may be implemented as any of the optical arrangements or optical indicators disclosed hereinabove and illustrated in any of the drawings or any suitable modification and/or variation thereof. The optical assembly 310 is configured to allow a fluid being tested or monitored for change to enter a suitable cavity (not shown in detail in the schematic block diagram of FIG. 13) formed therein. The optical assembly 310 may also be (optionally, but not obligatorily) configured to allow the fluid to exit the cavity formed therein through an (optional) fluid exit port or outlet (not shown in FIG. 13).

The cavity formed in the optical assembly 310 of the present invention is configured to function as a variable optical element when fully or partially filled with the fluid to be tested or monitored or checked.

A change in an optical property of the fluid within the cavity of the optical assembly such as the index of refraction or the rotation of the plane of polarization of light, or the like, may change the optical behavior or optical properties of the optical assembly 310 as explained in detail for the specific optical assemblies or arrangements disclosed hereinabove and illustrated in the drawings. For example, if the optical assembly 310 is configured as the enclosure 18 of FIG. 1, a change in the refractive index of the fluid disposed within the cavity 28 will change the magnification of the enclosure 18 (which functions in this particular case as a variable magnification lens). Similarly, if the optical assembly 310 is configured as the prismatic enclosure 52 of FIG. 2, a change in the refractive index of the fluid disposed within the bi-prismatic cavity 54 will change the refraction angle of beams of light by the prismatic enclosure 52 (which functions in this particular case as a variable deflection prismatic assembly). Such variable optical elements of the various embodiments of the invention are used in conjunction with other optical elements included in the optical assembly 310 (such as, for example, the pairs of gratings, the pairs of polarizers, collimating lenses, optical slits, stops, pinholes, apertures and the like, depending on the particular specific embodiment used), to project an image or pattern which may be different than the reference pattern used, as disclosed in detail hereinabove and illustrated in the drawings.

It is also noted that in accordance with certain embodiments of the present invention, the fluid included in the variable optical element's cavity, need not be a stationary fluid as the fluid may actually be flowing through the optical assembly's cavity, as disclosed hereinabove and illustrated in FIG. 12. Furthermore, the fluid may be a fluid disposed in the cavity for testing, and/or verification and/or authentication purposes, as disclosed hereinabove. For example, the fluid may be a non-authentic fluid (such as but not limited to a fake or non-authentic perfume that was fraudulently placed in an authentic perfume container which may include the variable optical element of the invention). Thus, the term "variable" as used in the term "variable optical element" herein, means that the optical element is designed or configured for varying it's optical properties if a fluid is disposed therein that has an optical parameter or property different than the same parameter or property of a known reference fluid. However, within the duration of an authentication procedure the optical property or parameter need not obligatorily change and it is only required that the optical property of the optical element is different than the same property if it was measured with the reference fluid (for which the optical element was pre-designed knowing the properties of the reference fluid beforehand) disposed in the same cavity. Thus, the use of the term "variable optical element" may mean, but does not obligatorily mean that the optical property of the element varies during the performing of an authentication or verification test, or the like.

The system 300 may also includes a (optional) source of light 12. The source of light 12 may be any suitable source of light that may produce diffused light having any suitable spectral content (including but not limited to polychromatic and monochromatic diffused light in the far and/or near infrared range, visible range and ultraviolet range, coherent light and non-coherent light, laser light, broadband light, or the like). Alternatively, in accordance with another embodiment of the present invention, the light source 12 may be omitted and the system may use available ambient diffused light. Furthermore, while use of diffused light may be preferred for certain embodiments of the present invention, the light used in the present invention need not obligatorily be diffused light and collimated light may also be used for other embodiments of the invention.

When the optical assembly 310 includes therein the fluid to be checked and/or monitored, the diffused light may enter the optical assembly and be modified by combination of the fluid filed cavity and other optical components of the optical assembly 310 as disclosed in detail hereinabove. The optical assembly 310 produces a modified optical signal that may be projected directly into a detecting unit 320. In accordance with one embodiment of the present invention, the detecting unit 320 may be the eye of a human observer, as disclosed in detail hereinabove. In such a case, the detection of change in the image produced by the optical assembly 310 may be visually done by the human user or observer.

In accordance with other embodiments of the invention, the detecting unit 320 may be implemented as a photo-detector (such as, but not limited to a photodiode, a photo-transistor, a photo-gate, a photoelectric cell, or the like), or a camera or an imager, or any other type of suitable photo-detector, or light sensitive device or imager or camera, or pixel-array known in the art. The detecting unit 320 may be suitably aligned with respect to the optical assembly 310 to receive the image produced by the optical assembly and may provide an output signal indicative of an image that is different than the reference image. The output signal may be any type of output signal known in the art such as an electrical output signal, a visible output signal, an audio output signal or any other output signal of any sensory modality or combination of sensory modalities.

The detecting unit 320 may also be (optionally) connected to a processing unit 330 for further processing of the output signals of the detecting unit 320. The processing unit may be implemented as or may include one or more of controller, microcontroller, processor, microprocessor, computer, personal computer, digital signal processor (DSP), analog signal processor, or any other type of suitable computing device. The processing unit 330 may further process the output signals of the detecting unit to provide an indication or an output signal indicative of a change or status of the fluid in the optical assembly 310.

Many different types of algorithms and or computer programs may be implemented in order to provide an indication of the state of the fluid in the optical assembly 310. Methods for distinguishing a pattern (such as, but not limited to, any of the moiré patterns or other patterns or images illustrated in the drawings indicative of a changed state of a fluid) from another different reference pattern, are well known in the art, are not the subject matter of the present application and are therefore not described in detail hereinafter.

Briefly, suitable algorithms or any software operative on the processing unit 330 may use any suitable image analysis methods or other numerical algorithms known in the art for comparing the image detected by the detecting unit 320 when the fluid is in a changed state to the image detected by the detecting unit 320 when the fluid is in a reference state. The processor unit 330 may have a look up table (LUT) or other types of stored data based on previous calibration measurements of the reference fluid or based on factory supplied predetermined data.

Alternatively, the processing unit 330 may process the image data or the detector unit's output based on predetermined or preset data or criteria or threshold values, or the like (such preset data or criteria or thresholds may themselves be based, inter alia, on the structure, configuration and optical properties of the optical assembly, and possibly on data of the reference properties and range of possible changes of the properties of the tested or checked fluid) which may enable the processing unit 330 to detect a certain preset or predetermined change in the fluid within the optical assembly 310, or even to compute the degree of change of the fluid's state relative to the reference state of the reference fluid.

It is noted that the output of the detector unit 320 or of the (optional) processing unit 330 may be a YES/NO type output, indicative of whether a change was detected in the state of the fluid, or may be a semi-quantitative output or a quantitative output proportional or indicative of the degree or intensity of the change that was detected.

Generally, any type of indication system or output signal system or display system known in the art may be used or combined with the system 300 for presenting or communicating the test results to the user of the system 300.

For example, the detecting unit 320 (or the processing unit 330) may light up a red light emitting diode (LED) if it detects or computes from the modified optical signal (the image) output by the optical assembly 310 that the milk in a storage tank has become sour (as described in detail hereinabove). In another example, the processing unit 330 may process the image data from the detecting unit 320 (possibly implemented as an active pixel CMOS imager) to determine or compute a quantitative (or a semi-quantitative) parameter or value representative of the state of the tested fluid, such as, but not limited to the refractive index of the fluid or the rotation of the plain of polarized light by the fluid, or any other parameter related to other detectable change(s) in the properties or state of the tested fluid. Such computed value or values may be presented to the user using any suitable presentation means or devices, such as for example, a display unit (not shown) displaying symbolic or numerical data or graphic data or textual data, or by an analogue or quasi-analog display methods such as a change of a color in accordance with a predetermined color scale, or a tone with varying frequency or the like.

It is however noted that the methods and devices used for communicating the test results to a user are not limited to those methods and devices described herein and that many other devices and/or methods known in the art may be used for implementing the system 300 of present invention, or any other systems disclosed herein.

It is noted that the optical assembly 310 of the system 300 may be configured for inserting (and removing, if necessary) the fluid from a single inlet/outlet port, as disclosed hereinabove and illustrated in the drawings (see, for example, FIG. 6B), or may be implemented as a flow-through configuration having an inlet fluid port and an outlet fluid port for systems in which the fluid flows through the optical assembly (see, for example, FIG. 6A).

It is further noted that, in accordance with another embodiment of the present invention, the breaking up of white light into constituent colors (wave dispersion) may be also used in the indicator of the present invention. For example, the transparent enclosure may be formed as a Newton prism (not shown) with a narrow beam of white light observed through a narrow slit (not shown). The beam will be decomposed into a few color beams, and depending on the current refraction coefficient of the monitored fluid, the observer will see one of the beams (one color) through the slit.

It will be appreciated by those skilled in the art that the devices systems and methods disclosed hereinabove are not limited to the particular arrangement illustrated in the drawings. Rather many variations and permutations of the optical arrangements and optical systems may be used in implementing various different embodiments of the present invention. Many parameters of the devices and systems of the invention may be varied, such as, but not limited to, the number and arrangement of the gratings used, their positions along the optical axis and/or relative to each other, their orientations relative to each other and relative to the other optical components, the exact shape, size and curvature and degree of the lenses used (including but not limited to the lenses 24, 26, 72, 74, 78, 88, 108) the refractive index of the various optical components of the described optical arrangements and the materials they are made of or the materials included therein.

In another example, while in certain configurations disclosed hereinabove the gratings are rotated relatively to the optical axis such that the rulings or lines of one of the gratings are inclined at an angle to the rulings or lines of the other grating to make the moiré pattern change more observable, this is not obligatory to practicing the invention and the rulings or lines of the gratings may be non-inclined (in such a case the observable pattern change may look different and may be observed as a phase change in the fringe pattern).

Furthermore, while some specific embodiments of the present invention are adapted to providing an indication of the state of a fluid or liquid, it will be appreciated that the devices and systems disclosed herein may be easily adapted without undue experimentation to detect and/or monitor tampering with or dilution of a liquid or fluid in a container or packaging and may also be used as a tamper detecting device to detect fake or diluted products or to detect defective products due to change in the fluid properties due to improper storage and/or expiry of the products shelf life, and/or exposure to undesirable conditions or chemicals or degrading exposure to light, or other similar changes in the product.

The invention may also be used for authenticating purposes for expensive or lucrative products such as perfumes, expensive alcoholic beverages, and the like, as described in detail hereinabove.

It is further noted that some or all of the parts of the components of the optical assemblies, and/or optical indicators, and/or optical arrangement usable as optical indicators of the present invention may be integrated with or formed from the actual walls or any other parts of a container or packaging which holds the fluid. For example, if gratings are used in implementing the optical indicator, the gratings may be formed on or within, or included in the walls of a liquid container, or other suitable parts or may be printed thereon or embossed on a wall or other suitable parts of the container by using any suitable method of manufacturing or forming as is known in the art (such as, but not limited to, printing molding, embossing, imprinting, and the like). Similarly, any prisms or cavities or enclosures or lenses or polarizers or collimators or any other of the optical parts included in the optical assemblies and/or systems of the optical indicators of the present invention may be formed as integral parts of the container or packaging of a fluid or may be suitably attached thereto by using any suitable manufacturing methods known in the art.

The invention may also be implemented to detect changes with fuel products or fuel, such as but not limited to, gasoline, or the like to detect dilution with other non-fuel liquids (water or the like) or to detect dilution or complete substitution of the tested fuel with low grade fuels.

Although a description of specific embodiments has been presented, it is contemplated that various changes could be made without deviating from the scope of the present invention. For example, the indicator of the present invention could be modified and used with ultraviolet or infrared light.

The invention claimed is:

1. An optical indicator for identification of a changed state of a fluid with respect to a reference state of said fluid, the fluid having an index of refraction changing with the change of the state of said fluid, said indicator being mountable to or integral with a container for said fluid and comprising:
   a) a transparent enclosure including a wall and a cavity in fluid communication with said container;
   b) an object comprising a pair of gratings at one side of said enclosure forming a reference moiré image;
   c) an optical system having an optical axis and enabling the observation of said object when illuminated by diffuse light, via said enclosure filled with said fluid;
   said optical indicator being designed such that an image of said object observed in the changed state of the fluid is optically distinctive from an image of said object observed in said reference state of the fluid.

2. The optical indicator of claim 1, wherein said pair of gratings are disposed in parallel planes.

3. The optical indicator of claim 1, wherein said wall is formed as an active optical element constituting part of said optical system.

4. The optical indicator of claim 3, wherein said optical element is an optical lens or prism.

5. The optical indicator of claim 3, wherein said cavity and said wall are formed such that, when said cavity is filled with said fluid in the reference state, said transparent enclosure constitutes a lens or a prism with predetermined optical power.

6. The optical indicator of claim 5, wherein said predetermined optical power is zero.

7. The optical indicator of claim 5, wherein said optical system comprises a lens and a pinhole so as to project said image on the retina of an observer's eye.

8. The optical indicator of claim 5, wherein said optical system comprises a collimating lens and an eye-piece lens.

9. The optical indicator of claim 5, wherein said wall of the transparent enclosure is formed as two concavo-convex lenses with said cavity defined between convex sides of said lenses.

10. The optical indicator of claim 5, wherein said wall of the transparent enclosure is formed as two concavo-convex lenses with said cavity defined between concave sides of said lenses.

11. The optical indicator of claim 5, wherein said cavity is formed as a double-wedge prism with said gratings at bases of the wedges of the double-wedge prism and with walls formed as two triangular prisms adjacent to either side of said double-wedge prism.

12. The optical indicator of claim 5, wherein said wall of the transparent enclosure is formed as a triangular prism with a base facing said optical system and with said cavity formed as two wedge prisms adjacent to either side of said triangular prism, said gratings being disposed at bases of said two wedge prisms.

13. The optical indicator of claim 1, wherein said pair of gratings are a pair of Ronchi rulings.

14. The optical indicator of claim 13, wherein a first set of Ronchi rulings in said pair are disposed at a sharp angle with respect to a second set of Ronchi rulings.

15. The optical indicator of claim 1, wherein said gratings comprise curved lines.

16. The optical indicator of claim 15, wherein said curved lines are concentric circles.

17. The optical indicator of claim 1, wherein said pair of gratings comprises at least two pairs of said gratings, each of the two pairs of gratings producing a moiré pattern such that said patterns can be observed superimposed or juxtaposed.

18. The optical indicator of claim 1, wherein said indicator is adapted for integral mounting in a closure of said container or in a pipe for transporting said fluid.

19. The optical indicator of claim 1, wherein said container is a package of drinkable liquid or liquid medication.

20. The optical indicator of claim 1, wherein said indicator is made of plastic material.

21. The optical indicator of claim 20, wherein said indicator is made of single molded piece of said plastic material.

22. The optical indicator of claim 20, wherein said plastic material is polycarbonate or cyclic olefin copolymer.

23. The optical indicator of claim 20, wherein said indicator is disposable.

24. The optical indicator of claim 1, further comprising a housing accommodating said enclosure and a transparent mask carrying said gratings and disposed transversely to said optical axis.

25. The optical indicator of claim 24, wherein said housing has a pinhole for observation of said object.

26. The optical indicator of claim 24, wherein said housing has a port for connecting to said container providing said fluid communication to said cavity.

27. The optical indicator of claim 24, wherein said indicator is integral with a cap of said container, said housing and said mask constituting portions of said cap.

28. The optical indicator of claim 24, wherein said container is a bottle with a neck and said optical indicator is mountable in said neck with said optic axis transverse thereto.

29. The optical indicator of claim 24, wherein said container is a portion of a pipeline or a fitting for transferring said fluid and said optical indicator is integral with said portion or a fitting such that at least part of said fluid passes through said cavity.

30. The optical indicator of claim 24, wherein said container is a bag for liquid medication.

31. The optical indicator of claim 30, wherein said bag is an infusion bag and said optical indicator is integral with an injection port of said infusion bag.

* * * * *